(12) United States Patent
He et al.

(10) Patent No.: US 11,847,094 B2
(45) Date of Patent: Dec. 19, 2023

(54) MEDICAL DEVICE AND DATA MANAGEMENT METHOD FOR SAME

(71) Applicant: SHENZHEN MINDRAY BIO-MEDICAL ELECTRONICS CO., LTD., Shenzhen (CN)

(72) Inventors: Yande He, Shenzhen (CN); Xin Xu, Shenzhen (CN); Xuyun Wang, Shenzhen (CN); Jinbo Ge, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 262 days.

(21) Appl. No.: 17/478,910

(22) Filed: Sep. 18, 2021

(65) Prior Publication Data
US 2022/0004523 A1 Jan. 6, 2022

Related U.S. Application Data

(63) Continuation-in-part of application No. PCT/CN2019/078864, filed on Mar. 20, 2019.

(51) Int. Cl.
*G06F 16/16* (2019.01)
*G06F 11/30* (2006.01)
(Continued)

(52) U.S. Cl.
CPC ........ *G06F 16/162* (2019.01); *G06F 11/3051* (2013.01); *G06F 11/3072* (2013.01); *G06F 2201/86* (2013.01)

(58) Field of Classification Search
CPC .......................... G06F 16/162; G06F 2201/86
See application file for complete search history.

(56) References Cited

U.S. PATENT DOCUMENTS

| 8,032,398 B1 | 10/2011 | Kelly et al. | |
| 2012/0253724 A1* | 10/2012 | Asai .................. | G05B 23/0235 702/128 |

(Continued)

FOREIGN PATENT DOCUMENTS

| CN | 204631870 U | 9/2015 |
| CN | 106778021 A | 5/2017 |

OTHER PUBLICATIONS

International Search Report issued in corresponding International Application No. PCT/CN2019/078864, dated Dec. 11, 2019, 4 pages.

*Primary Examiner* — Getente A Yimer
(74) *Attorney, Agent, or Firm* — BAYES PLLC

(57) ABSTRACT

Disclosed are a medical device and a data management method therefor. The data management method includes: receiving an instruction for selecting a locking rule to determine a target locking rule, wherein the target locking rule is used for screening monitoring data so as to carry out locking; under the trigger of a first trigger condition, screening the monitoring data according to the target locking rule, and locking the screened monitoring data; and under the trigger of a second trigger condition, selectively deleting monitoring data that is not locked. An operator can selectively lock the monitoring data by selecting the locking rule, thereby avoiding the deletion of monitoring data needing to be retained, and facilitating the management of the monitoring data.

20 Claims, 2 Drawing Sheets

(51) Int. Cl.
*G06F 16/215* (2019.01)
*G16H 10/00* (2018.01)

(56) References Cited

U.S. PATENT DOCUMENTS

| | | | |
|---|---|---|---|
| 2013/0346574 A1* | 12/2013 | Singaraju | H04L 41/046 |
| | | | 709/223 |
| 2015/0040215 A1* | 2/2015 | Blodgett | G06F 21/85 |
| | | | 726/22 |
| 2015/0339736 A1* | 11/2015 | Bennett | G06Q 30/0278 |
| | | | 705/306 |
| 2017/0103009 A1* | 4/2017 | Sanghvi | G06F 11/3096 |
| 2017/0372022 A1* | 12/2017 | Cuellar | G06F 21/6245 |
| 2019/0371157 A1* | 12/2019 | Judice | G01D 21/00 |

* cited by examiner

MEDICAL DEVICE AND DATA MANAGEMENT METHOD FOR SAME

CROSS REFERENCE TO RELATED APPLICATION

This application is a bypass continuation-in-part of Patent Cooperation Treaty Application No. PCT/CN2019/078864, filed on Mar. 20, 2019, the content of which is hereby incorporated by reference in its entirety.

TECHNICAL FIELD

The disclosure relates to the field of medical devices, and specifically to a medical device and a data management method for same.

BACKGROUND

Data storage and review are the most commonly used functions in a monitor and a central station. With the continuous monitoring of patients, more and more data need to be stored in the monitor and the central station, but the monitor and the central station have limited storage space and cannot store all the data. One solution is to implement the storage of patient history data by means of rewinding, that is, deleting data in order from old to new, and freeing up storage space to store the latest data. Although the latest data can be stored by using such a method, earlier data that is important or required by a user is also deleted.

SUMMARY

The disclosure mainly provides a medical device and a data management method for same, so as to reduce the risk of deleting monitoring data that needs to be retained.

An embodiment provides a method for managing monitoring data for a medical device, including:
  receiving an instruction for selecting a locking rule, to determine a target locking rule, where the locking rule is used to filter the monitoring data to facilitate locking;
  when a first trigger condition is satisfied, filtering the monitoring data according to the target locking rule, and locking the filtered monitoring data; and
  when a second trigger condition is satisfied, selectively deleting unlocked monitoring data.

An embodiment provides a medical device, including:
  a data obtaining module configured to obtain monitoring data;
  a human-machine interaction apparatus configured to receive an input of an operator and output visual information;
  a storage apparatus configured to store monitoring data; and
  a processor configured to receive, by means of the human-machine interaction apparatus, an instruction for selecting a locking rule, and determine a target locking rule according to the instruction, where the locking rule is used to filter the monitoring data to facilitate locking; when a first trigger condition is satisfied, filter the monitoring data according to the target locking rule, and lock the filtered monitoring data; and when a second trigger condition is satisfied, selectively delete unlocked monitoring data.

An embodiment provides a medical device, including:
  a data obtaining module configured to obtain monitoring data;
  a human-machine interaction apparatus configured to receive an input of an operator and output visual information;
  a storage apparatus configured to store monitoring data; and
  a memory configured to store a program, where the processor is configured to execute the program stored in the memory, to implement the method as described above.

An embodiment provides a computer-readable storage medium including a program, where the program is executable by a processor to implement the method as described above.

According to the medical device and the data management method thereof in the foregoing embodiments, an operator can selectively lock the monitoring data by selecting the locking rule, thereby avoiding the deletion of monitoring data that needs to be retained, and facilitating the operator in managing the monitoring data.

DETAILED DESCRIPTIONS

Figure 1:
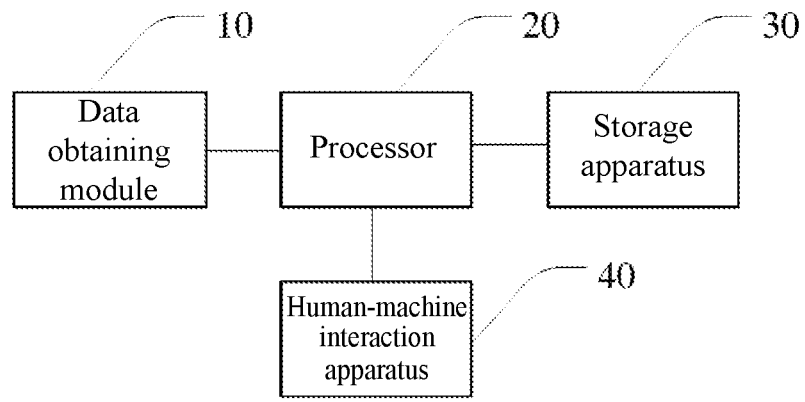
FIG. 1 is a structural block diagram of a medical device according to an embodiment.

The disclosure will be further described in detail below through specific implementations in conjunction with the accompanying drawings. Associated similar element reference numerals are used for similar elements in different implementations. In the following implementations, many details are described such that the disclosure may be better understood. However, it may be effortlessly appreciated by persons skilled in the art that some of the features may be omitted, or may be substituted by other elements, materials, and methods in different cases. In certain cases, some operations involved in the disclosure are not displayed or described in the specification, which is to prevent a core part of the disclosure from being obscured by too much description. Moreover, for persons skilled in the art, the detailed description of the involved operations is not necessary, and the involved operations can be thoroughly understood according to the description in the specification and general technical knowledge in the art.

In addition, the characteristics, operations, or features described in the specification may be combined in any appropriate manner to form various implementations. Meanwhile, the steps or actions in the method description may also be exchanged or adjusted in order in a way that is obvious to persons skilled in the art. Therefore, the various orders in the specification and the accompanying drawings are merely for the purpose of clear description of a certain embodiment and are not meant to be a necessary order unless it is otherwise stated that a certain order must be followed.

The serial numbers themselves for the components herein, for example, "first" and "second", are merely used to distinguish described objects, and do not have any sequential or technical meaning. Moreover, as used in the disclosure, "connection" or "coupling", unless otherwise stated, includes both direct and indirect connections (couplings).

The disclosure mainly relates to the management of monitoring data generated by a monitor, so that monitoring data that needs to be retained is stored as much as possible. As shown in FIG. 1, a medical device provided in the disclosure, such as a monitor or a central station (central monitoring system), includes a data obtaining module 10, a processor 20, a storage apparatus 30, and a human-machine interaction apparatus 40. In this embodiment, a central station is taken as an example of the medical device for description.

The data obtaining module 10 is configured to obtain monitoring data, and is configured to obtain monitoring data from a monitor in some examples. The monitoring data may be generated by the monitor in the process of monitoring a patient, such as an alarm event, a rescue event, an EWS score, medication taken, a physiological parameter of the patient (such as one or more of electrocardiogram, respiration, non-invasive blood pressure, blood oxygen saturation, pulse, body temperature, invasive blood pressure, end-tidal carbon dioxide, respiratory mechanics, anesthetic gas, cardiac output, and electroencephalogram bispectral index), data input by medical care personnel to the monitor (for example, after rescue), etc. In some embodiments, the data obtaining module 10 can be sensors for acquiring the monitoring data. In some embodiments, the data obtaining module 10 can be a communication port to receive the obtained monitoring data.

The human-machine interaction apparatus 40 is configured to receive an input of an operator and output visual information. For example, a touchscreen may be used, which can not only receive an instruction input by the operator, but also can display visual information; alternatively, a mouse, a keyboard, a trackball, a joystick, etc. may be used as an input apparatus of the human-machine interaction apparatus 40 to receive an instruction input by the operator, and a display may be used as a display apparatus of the human-machine interaction apparatus 40 to display visual information.

The storage apparatus 30 is configured to store the monitoring data.

The processor 20 is configured to: display at least one locking rule in a display interface of the human-machine interaction apparatus 40 for the operator to select, receive, by means of the human-machine interaction apparatus 40, an instruction for selecting a locking rule to determine a target locking rule according to the instruction; when a first trigger condition is satisfied, filter the monitoring data according to the target locking rule, and lock the filtered monitoring data; and when a second trigger condition is satisfied, selectively delete unlocked monitoring data. It can be seen that because the unlocked monitoring data is selectively deleted, the operator can selectively lock the monitoring data by selecting the locking rule, thereby avoiding the deletion of the monitoring data that needs to be retained, and facilitating the operator in managing the monitoring data.

Figure 2:
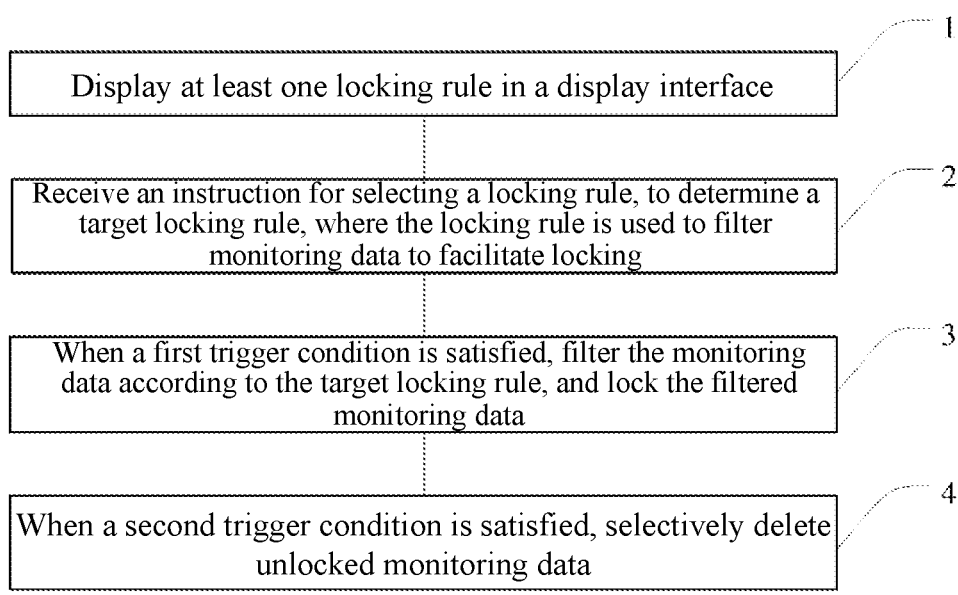
FIG. 2 is a flowchart of a data management method for a medical device according to an embodiment.

FIG. 2 shows a process for managing the monitoring data. That is, the processor 20 may further implement a method for managing the monitoring data provided in an embodiment of the disclosure. Some steps are as follows.

At step 1, the processor 20 displays at least one locking rule in a display interface of the human-machine interaction apparatus 40 for the operator to select. The locking rule is used to filter the monitoring data to facilitate locking. It can be seen that the operator can select a corresponding locking rule to avoid the deletion of corresponding monitoring data, and the operation is very convenient. Some locking rules are rules for locking according to an alarm event, that is, the monitoring data is filtered according to an alarm event to facilitate locking. Some locking rules are rules for locking according to a rescue event, that is, the monitoring data is filtered according to a rescue event to facilitate locking. Some locking rules are rules for locking according to an EWS score, that is, the monitoring data is filtered according to an EWS score to facilitate locking. Some locking rules are rules for locking according to medication taken, that is, the monitoring data is filtered according to medication taken to facilitate locking.

At step 2, the processor 20 receives, by means of the human-machine interaction apparatus 40, an instruction for selecting a locking rule to determine a target locking rule. The operator needs to select a corresponding locking rule by means of the human-machine interaction apparatus 40, such that the processor 20 can determine the target locking rule.

At step 3, when a first trigger condition is satisfied, the processor 20 filters the monitoring data according to the target locking rule, and locks the filtered monitoring data. Alternatively, the operator may also manually lock the monitoring data. For example, the human-machine interaction apparatus 40 is used to receive an instruction for selecting the monitoring data to further lock the selected monitoring data. The first trigger condition includes at least one of the following three conditions: 1. new monitoring data is obtained; 2. a current moment is a trigger moment of a preset interval trigger; and 3. a trigger instruction input by an operator is received. By setting the first trigger condition, the processor 20 may filter, according to the target locking rule selected by the operator, the monitoring data when the new monitoring data is obtained, and lock the filtered monitoring data; or may filter the monitoring data and lock the filtered monitoring data after a specific time interval; or may filter the monitoring data and lock the filtered monitoring data after the operator manually issues an instruction. The new monitoring data may be monitoring data of a new patient, or may be newly generated monitoring data of the patient being monitored.

Further, the monitoring data filtered based on the target locking rule may further be stored separately in a storage location corresponding to the target locking rule. In some embodiments, the filtered monitoring data may be presented in the form of folder content according to user needs. For example, there are currently several locking rules, and each locking rule is used to lock corresponding monitoring data. When each locking rule may be correspondingly stored with the corresponding monitoring data locked by using the locking rule, the processor may filter, based on the needs of a user A, one or more pieces of monitoring data from the corresponding monitoring data locked by using each locking rule, to form monitoring data favorites obtained based on the needs of the user A. In this way, the user may browse, based on the locking rule, the corresponding monitoring data locked using the locking rule, or may view, in the form of favorites based on his/her own needs, the locked monitoring data required by the user. In other words, each locking rule can ensure that important monitoring data can be locked, thereby avoiding deletion; and favorites set based on the needs of the user can present each piece of locked monitoring data according to the needs of the user.

In one embodiment, the human-machine interaction apparatus 40 is provided with favorites button, and the user may add any monitoring data to the favorites by means of the human-machine interaction apparatus 40. The monitoring data that has been locked based on each locking rule may be directly added to the favorites of the current user. When selected as a favorite by the user, the monitoring data that is not locked based on the locking rule will be locked based on the current add-to-favorites operation and then added to favorites. When there is a target locking rule, the monitoring data is locked based on the target locking rule. Alternatively, when there is no target locking rule, the monitoring data selected by the user may be locked based on the add-to-favorites operation.

When a favorites instruction from the user is received, corresponding monitoring data selected by the favorites instruction is added to a storage location corresponding to the favorites instruction, for example, a favorites folder or an interface presented in the form of a folder in the display interface. In addition, the favorites instruction may further carry a user identity that specifies a favorites rule, and different favorites may be generated based on user identities. For example, different favorites may be generated based on identities of medical care personnel, e.g., "Dr. Zhang's favorites" and "Nurse Li's favorites", or may be generated based on user identities, e.g., "Patient A's favorites" and "Patient B's favorites", or the like. In this way, the favorites may be set based on the needs of the user, so as to improve the work efficiency of the user.

At step 4, when a second trigger condition is satisfied, the processor 20 selectively deletes unlocked monitoring data. For example, the unlocked monitoring data is selectively deleted to free up storage space for storing new monitoring data, and the new monitoring data is stored after being obtained, thereby not only retaining the locked monitoring data but also freeing up the storage space to realize high utilization of the storage apparatus 30. For another example, the unlocked monitoring data may be selectively deleted in order according to storage times from longest to shortest, so that newer monitoring data can be stored for a longer time.

Figure 3:
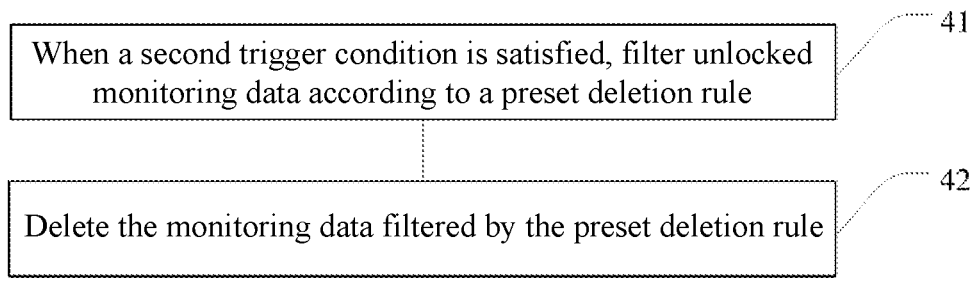
FIG. 3 is a specific flowchart of step 4 in FIG. 2.

As shown in FIG. 3, in this embodiment, step 4 may include the following steps S41-S42.

At step 41, when the second trigger condition is satisfied, the unlocked monitoring data may be filtered according to a preset deletion rule. The preset deletion rule may be embedded in the medical device, or may be selected by the operator. In this embodiment, the latter is taken as an example for description. For example, at least one deletion rule is displayed in the display interface of the human-machine interaction apparatus 40 for the operator to select, and an instruction for selecting a deletion rule is received, so as to determine a target deletion rule. The deletion rule is used to filter the monitoring data to facilitate deletion. When the second trigger condition is satisfied, the unlocked monitoring data is filtered according to the target deletion rule. The unlocked monitoring data may be filtered according to the target deletion rule in two manners. One is that the processor 20 determines whether the monitoring data stored in the storage apparatus 30 is locked, to filter out all unlocked monitoring data, and then filters the unlocked monitoring data according to the target deletion rule. The other is that the processor 20 filters out the monitoring data according to the target deletion rule, and then determines whether the filtered monitoring data is locked, to obtain the unlocked monitoring data that conforms to the target deletion rule.

At step 42, the monitoring data filtered by the preset deletion rule may be deleted. That is, in this embodiment, the monitoring data filtered by the target deletion rule is deleted.

The second trigger condition includes at least one of the following four conditions: 1. new monitoring data is obtained; 2. a current moment is a trigger moment of a preset interval trigger; 3. a trigger instruction input by an operator is received; and 4. the storage apparatus 30 has no remaining storage capacity for new monitoring data. That is, by setting the second trigger condition, the processor 20 may filter, according to the target deletion rule selected by the operator, the monitoring data when the new monitoring data is obtained, and delete the filtered monitoring data; or may filter the monitoring data and delete the filtered monitoring data after a specific time interval; or may filter the monitoring data and delete the filtered monitoring data after the operator manually issues an instruction; or may filter the monitoring data and delete the filtered monitoring data after the storage of the storage apparatus 30 becomes full.

In some embodiments, the processor 20 is further configured to determine, by means of the human-machine interaction apparatus 40, a network storage address set by the operator, and upload, according to the network storage address set by the operator, the monitoring data to be deleted to the network storage address for storage before the monitoring data is deleted. Such a setting can achieve remote retention of the deleted monitoring data.

Figure 4:
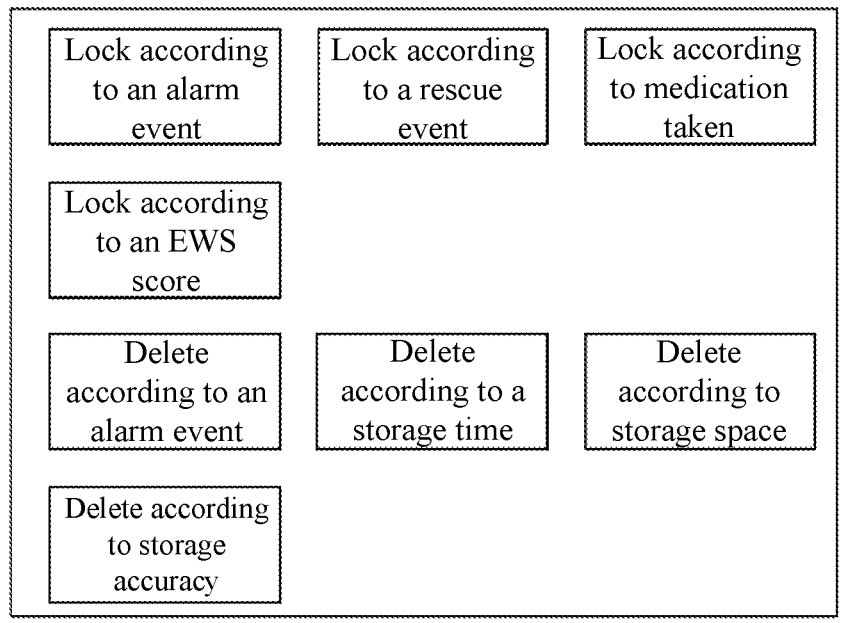
FIG. 4 is a schematic diagram of a setting interface of a medical device according to an embodiment.

A further description is provided below with reference to some application scenarios. As shown in FIG. 4, the operator enters a setting interface by operating the human-machine interaction apparatus 40, and a plurality of locking rules and a plurality of deletion rules are displayed on the setting interface for the operator to select. Alternatively, in some embodiments, the locking rules and the deletion rules may also be displayed in different display interfaces. The locking rules and the deletion rules displayed may be abstract information of the rules or may be all content of the rules. For example, the abstract information of the rules is displayed, after the operator selects or clicks, the display interface may also switch to a next sub-page to display some further settings. For example, after the locking rule of locking according to an alarm event is selected, a specific alarm event (such as a fatal arrhythmia alarm) is displayed on the next sub-page for the operator to select.

After the target locking rule is determined through selection or setting by the operator, the data obtaining module 10 obtains new monitoring data from the medical monitor. When the target locking rule is locking according to an alarm event, the processor 20 determines whether the new monitoring data includes an alarm event and whether the alarm event included in the new monitoring data belongs to the alarm event (such as the fatal arrhythmia alarm) selected by the operator in the target locking rule when the new monitoring data is determined to include an alarm event. When the determined alarm event belongs to the alarm event selected by the operator in the target locking rule, the alarm event of the new monitoring data, or the new monitoring data, or all monitoring data of the patient corresponding to the new monitoring data may be locked and stored in the storage apparatus 30. Otherwise, the new monitoring data is directly stored in the storage apparatus 30. Alternatively, in some embodiments, after the data obtaining module 10 obtains the new monitoring data, the new monitoring data may also be first stored, and then the determination is performed.

If the target locking rule is locking according to a rescue event, the processor 20 determines whether the new monitoring data includes a rescue event, and locks the rescue event of the new monitoring data, the new monitoring data, or all monitoring data of the patient corresponding to the new monitoring data when the new monitoring data is determined to include a rescue event, and stores the locked new monitoring data in the storage apparatus 30. If the new monitoring data does not include a rescue event, the new monitoring data is directly stored in the storage apparatus

30. Alternatively, in some embodiments, after the data obtaining module 10 obtains the new monitoring data, the new monitoring data may also be first stored, and then the determination is performed.

If the target locking rule is locking according to medication taken, the processor 20 determines whether the new monitoring data includes medication taken by the patient. When the new monitoring data is determined to include medication taken by the patient, the processor 20 determines whether the medication taken by the patient is preset medication; and if the medication taken by the patient is the preset medication, the processor 20 locks the medication information in the new monitoring data, or locks the new monitoring data, or locks all monitoring data of the patient corresponding to the new monitoring data. After being locked, the new monitoring data is stored. Otherwise, when there is no medication information in the new monitoring data, the new monitoring data is directly stored in the storage apparatus 30. Alternatively, in some embodiments, after the data obtaining module 10 obtains the new monitoring data, the new monitoring data may also be first stored, and then the determination is performed. The preset medication may be preset by the operator or may be embedded in the system.

If the target locking rule is locking according to an EWS score (early warning score), the processor 20 determines whether the new monitoring data includes an EWS score, and whether the EWS score exceeds a preset score (for example, 5 points) when the new monitoring data includes an EWS score. When the EWS score is determined to exceed the preset score, the processor may lock the EWS score for the new monitoring data, or lock the new monitoring data, or lock all monitoring data of the patient corresponding to the new monitoring data. After being locked, the new monitoring data is stored. Otherwise, the new monitoring data is stored in the storage apparatus 30. Alternatively, in some embodiments, after the data obtaining module 10 obtains the new monitoring data, the new monitoring data may also be first stored, and then the determination is performed.

After obtaining the new monitoring data from the medical monitor, the data obtaining module 10 stores the new monitoring data in the storage apparatus 30. When a current moment is a trigger moment of a preset interval trigger, or after a trigger instruction input by the operator is received, if the target locking rule is locking according to an alarm event, the processor 20 determines whether all monitoring data stored in the storage apparatus 30 includes an alarm event, or determines whether the monitoring data stored in the storage apparatus 30 from a previous locking moment to the current moment includes an alarm event. When the monitoring data includes an alarm event, the processor 20 determines whether the alarm event belongs to the alarm event (such as the fatal arrhythmia alarm) selected by the operator in the target locking rule; and when the alarm event belongs to the alarm event selected by the operator in the target locking rule, the processor 20 may lock the alarm event, or lock all monitoring data of the patient corresponding to the alarm event.

If the target locking rule is locking according to a rescue event, the processor 20 determines whether all monitoring data stored in the storage apparatus 30 includes a rescue event, or determines whether the monitoring data stored in the storage apparatus 30 from a previous locking moment to the current moment includes a rescue event. When the monitoring data includes a rescue event, the processor 20 may lock the rescue event, or lock all monitoring data of the patient in the rescue event.

If the target locking rule is locking according to medication taken by the patient, the processor 20 determines whether all monitoring data stored in the storage apparatus 30 includes medication taken by the patient, or determines whether the monitoring data stored in the storage apparatus 30 from a previous locking moment to the current moment includes medication taken by the patient. When the monitoring data includes the medication taken by the patient, the processor 20 determines whether the medication taken by the patient is preset medication, and locks the medication or all monitoring data of the patient taking the medication when the medication taken by the patient is the preset medication.

If the target locking rule is locking according to an EWS score (early warning score), the processor 20 determines whether all monitoring data stored in the storage apparatus 30 includes an EWS score, or determines whether the monitoring data stored in the storage apparatus 30 from a previous locking moment to the current moment includes an EWS score. When the monitoring data includes the EWS score, the processor 20 determines whether the EWS score exceeds a preset score (for example, 5 points), and locks the EWS score or all monitoring data of the patient corresponding to the EWS score when the EWS score exceeds the preset score.

The processor 20 is further configured to receive, by means of the human-machine interaction apparatus 40, an instruction for unlocking, to unlock the monitoring data. For example, the operator deselecting the target locking rule may be used as an unlocking instruction, and after the target locking rule is deselected, the locked monitoring data corresponding to the target locking rule is unlocked. For another example, in an display interface for unlocking, the operator unlocks the monitoring data by selecting the locked monitoring data. For still another example, in a monitoring data browsing interface, the monitoring data is selected by means of the human-machine interaction apparatus 40, and the selected monitoring data may be locked or unlocked through further operation, and so on.

After the target deletion rule is determined through the selection or setting by the operator, the monitoring data is deleted according to the target deletion rule. W the target deletion rule is deleting according to an alarm event, the processor 20 may filter the monitoring data according to alarm event levels in order from lowest to highest, so as to delete an alarm event with a lowest level. When the second trigger condition is satisfied, and for example, the storage apparatus 30 has no remaining storage capacity for new monitoring data, the processor 20 compares the levels of the alarm events stored in the storage apparatus 30 to obtain the alarm event with the lowest level, determines whether a network storage address is set, and stores the unlocked alarm event with the lowest level to the network storage address when the network storage address is set, and then deletes the unlocked alarm event. When no network storage address is set, the processor 20 may directly delete the unlocked alarm event with the lowest level to free up the storage space of the storage apparatus 30. The new monitoring data obtained can then be stored in the storage apparatus 30.

When the target deletion rule is deleting according to a storage time, e.g., according to an allowable storage time set by the operator, the processor 20 may filter out and deleting the monitoring data that has been stored for more than the allowable storage time. When the second trigger condition is satisfied, and for example, the storage apparatus 30 has no remaining storage capacity for new monitoring data, the processor 20 determines whether unlocked monitoring data stored in the storage apparatus 30 has been stored for more than the allowable storage time and whether a network storage address is set when the unlocked monitoring data has been stored for more than the allowable storage time. When the network storage address is set, the processor 20 may store the monitoring data to the network storage address and then deletes the monitoring data; otherwise, the processor 20 directly deletes the monitoring data to free up the storage space of the storage apparatus 30. The new monitoring data can then be stored in the storage apparatus 30. It can be seen that the locking rule and the deletion rule may be understood as two related factors. For example, deleting the monitoring data that has been stored for more than the allowable storage time may actually be changed to locking the monitoring data for the allowable storage time.

If the target deletion rule is deleting according to storage space, e.g., according to allowable storage space set by the operator, the processor 20 may filter out and delete the monitoring data that occupies more than the allowable storage space. The monitoring data of the same patient increases over time, and thus when the second trigger condition is satisfied, and for example, the storage apparatus 30 has no remaining storage capacity for new monitoring data, the processor 20 determines whether the unlocked monitoring data of the patient stored in the storage apparatus 30 occupies more than the allowable storage space. When the unlocked monitoring data occupies more than the allowable storage space, the processor 20 determines whether a network storage address is set; and stores the monitoring data of the patient to the network storage address when the network storage address is set, and then deletes the monitoring data. When there is no network storage address, the processor 20 may directly delete the monitoring data of the patient to free up the storage space of the storage apparatus 30. The obtained new monitoring data is stored in the storage apparatus 30.

If the target deletion rule is deleting according to storage accuracy, e.g., according to maximum storage waveform accuracy set by the operator, the processor 20 filters out the monitoring data having waveform accuracy higher than the maximum storage waveform accuracy, so as to delete a part of waveform of the monitoring data and reduce the waveform accuracy of the monitoring data. As the monitoring time passes, the importance of accuracy of earlier monitoring data of the patient decreases. When the second trigger condition is satisfied, and for example, the storage apparatus 30 has no remaining storage capacity for new monitoring data, the processor 20 determines whether the waveform accuracy of the unlocked monitoring data stored in the storage apparatus 30 is higher than the maximum storage waveform accuracy. When the waveform accuracy is higher than the maximum storage waveform accuracy, the processor 20 determines whether a network storage address is set; stores the monitoring data to the network storage address when the network storage address is set, and then deletes a part of waveform of the monitoring data to reduce the waveform accuracy of the monitoring data to the maximum storage waveform accuracy or below. When no network storage address is set, the processor 20 directly deletes a part of waveform of the monitoring data to reduce the waveform accuracy of the monitoring data to the maximum storage waveform accuracy or below, thereby freeing up the storage space of the storage apparatus 30. The obtained new monitoring data is then stored in the storage apparatus 30.

If the operator does not select the deletion rule, when the second trigger condition is satisfied, the processor may delete the unlocked monitoring data in order according to storage times from longest to shortest, so as to free up the storage space of the storage apparatus 30. After being obtained, the new monitoring data can be stored in the storage apparatus 30. Alternatively, when the operator selects the deletion rule for the unlocked monitoring data, the processor may still delete the unlocked monitoring data according to storage times in order from longest to shortest, so as to free up the storage space of the storage apparatus 30.

To avoid a conflict between the locking rule and the deletion rule, a priority of locking the monitoring data is higher than a priority of deleting the monitoring data.

It can be seen that the operator can clean up relatively unimportant monitoring data by selecting the deletion rule, to free up storage space for the new monitoring data; and can lock the required monitoring data by selecting the locking rule, to prevent the monitoring data from being deleted.

This embodiment further provides a method for managing monitoring data for a medical device. The method includes: obtaining new monitoring data; determining target monitoring data to be deleted, according to a preset deletion rule, where the preset deletion rule is used at least to determine an order of deleting the monitoring data; when it is determined based on a preset locking rule that the target monitoring data is locked, redetermining new target monitoring data according to the preset deletion rule; or when it is determined based on a preset locking rule that the target monitoring data is unlocked, deleting the target monitoring data to free up storage space for storing the new monitoring data; and storing the new monitoring data.

Persons skilled in the art may understand that all or some of the functions of the various methods in the above implementations may be implemented by means of hardware or by means of a computer program. When all or some of the functions in the above implementations are implemented by means of a computer program, the program may be stored in a computer-readable storage medium, and the storage medium may include: a read-only memory, a random access memory, a magnetic disk, an optical disk, a hard disk, and the like, and the program is executed by a computer to implement the above functions. For example, the program is stored in a memory of an apparatus, and when the program in the memory is executed by means of a processor, all or some of the above functions can be implemented. In addition, when all or some of the functions in the above implementations are implemented by means of a computer program, the program may also be stored in a storage medium such as a server, another computer, a magnetic disk, an optical disk, a flash disk, or a mobile hard disk, may be saved in a memory of a local apparatus through downloading or copying, or version updating may be performed on a system of the local apparatus. When the program in the memory is executed by means of a processor, all or some of the functions in the above implementations can be implemented.

The description has been made with reference to various exemplary embodiments herein. However, persons skilled in the art would have appreciated that changes and modifications could have been made to the exemplary embodiments without departing from the scope herein. For example, various operation steps and assemblies for executing operation steps may be implemented in different ways according to a specific application or considering any number of cost functions associated with the operation of the system (for example, one or more steps may be deleted, modified or incorporated into other steps).

In addition, as understood by persons skilled in the art, the principles herein may be reflected in a computer program product on a computer-readable storage medium that is pre-installed with computer-readable program code. Any tangible, non-transitory computer-readable storage medium can be used, including magnetic storage devices (hard disks, floppy disks, etc.), optical storage devices (CD-ROM, DVD, Blu Ray disks, etc.), flash memories, and/or the like. These computer program instructions can be loaded onto a general-purpose computer, a dedicated computer, or other programmable data processing apparatus to form a machine, such that these instructions executed on a computer or other programmable data processing apparatus can generate an apparatus that implements a specified function. These computer program instructions can also be stored in a computer-readable memory that can instruct a computer or other programmable data processing apparatus to operate in a specific manner, such that the instructions stored in the computer-readable memory can form a manufactured product, including an implementation apparatus that implements a specified function. The computer program instructions may also be loaded onto a computer or other programmable data processing apparatus, such that a series of operating steps are executed on the computer or other programmable device to produce a computer-implemented process, such that the instructions executed on the computer or other programmable device can provide steps for implementing a specified function.

Although the principles herein have been shown in various embodiments, many modifications of structures, arrangements, ratios, elements, materials, and components that are particularly suitable for specific environments and operating requirements can be made without departing from the principles and scope of the disclosure. The above modifications and other changes or amendments will be included within the scope herein.

The above specific description has been described with reference to various embodiments. However, persons skilled in the art would have appreciated that various modifications and changes could have been made without departing from the scope of the disclosure. Therefore, consideration of the disclosure will be in an illustrative rather than a restrictive sense, and all such modifications will be included within the scope thereof. Likewise, the advantages of various embodiments, other advantages, and the solutions to problems have been described above. However, the benefits, advantages, solutions to problems, and any elements that can produce these, or solutions that make them more explicit, should not be interpreted as critical, necessary, or essential. The term "comprise", "include", and any other variants thereof used herein are non-exclusive, so that the process, method, document, or device that includes a list of elements includes not only these elements, but also other elements that are not explicitly listed or do not belong to the process, method, system, document, or device. Furthermore, the term "coupling" and any other variations thereof used herein refer to physical connection, electrical connection, magnetic connection, optical connection, communication connection, functional connection, and/or any other connection.

Persons skilled in the art will recognize that many changes may be made to the details of the above-described embodiments without departing from the basic principles of the disclosure. Therefore, the scope of the disclosure should be determined according to the claims as follows.

What is claimed is:

1. A method for managing monitoring data for a medical device, comprising:
   receiving an instruction for selecting a locking rule, to determine a target locking rule, wherein the target locking rule is used to filter the monitoring data to facilitate locking;
   when a first trigger condition is satisfied, filtering the monitoring data according to the target locking rule, and locking the filtered monitoring data; and
   when a second trigger condition is satisfied, selectively deleting unlocked monitoring data.

2. The method of claim 1, further comprising:
   receiving a favorites instruction for adding monitoring data to favorites; and
   adding monitoring data selected by the favorites instruction to a storage location corresponding to the favorites instruction, or adding monitoring data selected by the favorites instruction to a display interface corresponding to the favorites instruction.

3. The method of claim 2, further comprising: when the monitoring data selected by the favorites instruction is not locked by using any locking rule, locking the monitoring data selected by the favorites instruction, to prevent the monitoring data selected by the favorites instruction from being deleted.

4. The method of claim 2, wherein the favorites instruction comprises a favorites rule, and monitoring data with a same favorites rule is stored in a same storage location, or the monitoring data with a same favorites rule is presented in a same display interface.

5. The method of claim 1, wherein before receiving the instruction for selecting the locking rule to determine the target locking rule, the method further comprises: displaying at least one locking rule in a display interface of the medical device for an operator to select.

6. The method of claim 2, wherein the locking rule comprises: filtering the monitoring data according to an alarm event, a rescue event, an EWS score, or medication taken.

7. The method of claim 1, wherein the first trigger condition and the second trigger condition each comprise at least one of the following three conditions:
   new monitoring data is obtained;
   a current moment is a trigger moment of a preset interval trigger; and
   a trigger instruction input by an operator is received.

8. The method of claim 1, further comprising receiving an instruction for selecting monitoring data and locking the selected monitoring data.

9. The method of claim 1, wherein selectively deleting unlocked monitoring data comprises: selectively deleting the unlocked monitoring data to free up storage space for storing new monitoring data; and storing the new monitoring data after the new monitoring data is obtained.

10. The method of claim 1, wherein selectively deleting unlocked monitoring data comprises: for the unlocked monitoring data, deleting the unlocked monitoring data in order according to storage times from longest to shortest.

11. The method of claim 1, wherein selectively deleting unlocked monitoring data comprises:
    filtering the unlocked monitoring data according to a preset deletion rule; and
    deleting the monitoring data filtered by the preset deletion rule.

12. The method of claim 11, wherein the preset deletion rule comprises:
    filtering out the monitoring data according to alarm event levels in order from lowest level to highest level, so as to delete an alarm event with a lowest level; or filtering out and deleting, according to an allowable storage time set by an operator, monitoring data that has been stored for more than the allowable storage time; or filtering out and deleting, according to allowable storage space set by an operator, monitoring data that occupies more than the allowable storage space; or filtering out, according to maximum storage waveform accuracy set by an operator, monitoring data having waveform accuracy higher than the maximum storage waveform accuracy, so as to delete a part of waveform of the monitoring data to reduce the waveform accuracy of the monitoring data, wherein a priority of locking the monitoring data is higher than a priority of deleting the monitoring data.

13. The method of claim 1, further comprising uploading, according to a network storage address set by an operator, the monitoring data to be deleted to the network storage address before deleting the monitoring data.

14. A medical device, comprising:
a data obtaining module configured to obtain monitoring data;
a human-machine interaction apparatus configured to receive an input of an operator and output visual information;
a storage apparatus configured to store monitoring data; and
a processor configured to:
receive, by means of the human-machine interaction apparatus, an instruction for selecting a locking rule, and determine a target locking rule according to the instruction, wherein the target locking rule is used to filter monitoring data to facilitate locking;
when a first trigger condition is satisfied, filter the monitoring data according to the target locking rule, and lock the filtered monitoring data; and
when a second trigger condition is satisfied, selectively delete unlocked monitoring data.

15. The medical device of claim 14, wherein the processor is further configured to: display at least one locking rule in a display interface of the human-machine interaction apparatus for an operator to select.

16. The medical device of claim 14, wherein the locking rule comprises: filtering the monitoring data according to an alarm event, a rescue event, an EWS score, or medication taken.

17. The medical device of claim 14, wherein the first trigger condition and the second trigger condition each comprise at least one of the following three conditions:
new monitoring data is obtained;
a current moment is a trigger moment of a preset interval trigger; and
a trigger instruction input by an operator is received by the human-machine interaction apparatus.

18. The medical device of claim 14, wherein the processor is further configured to:
selectively delete the unlocked monitoring data to free up storage space for storing new monitoring data; and store the new monitoring data after the new monitoring data is obtained;
or, for the unlocked monitoring data, delete the monitoring data in order according to storage times from longest to shortest;
or, filter the unlocked monitoring data according to a preset deletion rule; and delete the unlocked monitoring data filtered by the preset deletion rule.

19. The medical device of claim 18, wherein according to the preset deletion rule, the processor is configured to:
filter out the monitoring data according to alarm event levels in order from lowest level to highest level, so as to delete an alarm event with a lowest level; or
filtering out and deleting, according to an allowable storage time set by an operator, monitoring data that has been stored for more than the allowable storage time; or
filtering out and deleting, according to allowable storage space set by an operator, monitoring data that occupies more than the allowable storage space; or
filtering out, according to maximum storage waveform accuracy set by an operator, monitoring data having waveform accuracy higher than the maximum storage waveform accuracy, so as to delete a part of waveform of the monitoring data and reduce the waveform accuracy of the monitoring data,
wherein a priority of locking the monitoring data is higher than a priority of deleting the monitoring data.

20. The medical device of claim 14, wherein the processor is further configured to upload, according to a network storage address set by an operator, the monitoring data to be deleted to the network storage address for storage before the monitoring data is deleted.

* * * * *